(12) United States Patent
Akizuki et al.

(10) Patent No.: US 10,015,968 B2
(45) Date of Patent: Jul. 10, 2018

(54) METHOD FOR CONTROLLING ARTHROPOD PESTS

(71) Applicant: Sumitomo Chemical Company, Limited, Tokyo (JP)

(72) Inventors: Naoya Akizuki, Kasai (JP); Atsushi Iwata, Walnut Creek, CA (US); Yasutaka Shimokawatoko, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 15/305,858

(22) PCT Filed: Apr. 13, 2015

(86) PCT No.: PCT/JP2015/061329
§ 371 (c)(1),
(2) Date: Oct. 21, 2016

(87) PCT Pub. No.: WO2015/163177
PCT Pub. Date: Oct. 29, 2015

(65) Prior Publication Data
US 2017/0042158 A1    Feb. 16, 2017

(30) Foreign Application Priority Data

Apr. 24, 2014  (JP) ................ 2014-089866

(51) Int. Cl.
| | |
|---|---|
| A01B 49/06 | (2006.01) |
| A01C 1/08 | (2006.01) |
| A01C 5/00 | (2006.01) |
| A01C 21/00 | (2006.01) |
| A01M 1/20 | (2006.01) |
| A01N 25/00 | (2006.01) |
| A01N 43/78 | (2006.01) |
| A01N 43/88 | (2006.01) |
| A01N 47/44 | (2006.01) |
| A01N 51/00 | (2006.01) |

(52) U.S. Cl.
CPC .............. *A01N 51/00* (2013.01); *A01B 49/06* (2013.01); *A01C 1/08* (2013.01); *A01C 5/00* (2013.01); *A01C 21/00* (2013.01); *A01M 1/20* (2013.01); *A01N 25/00* (2013.01); *A01N 43/78* (2013.01); *A01N 43/88* (2013.01); *A01N 47/44* (2013.01)

(58) Field of Classification Search
CPC ......... A01B 49/06; A01B 49/04; A01B 49/00; A01C 1/08; A01C 1/00; A01C 5/00; A01C 21/00; A01M 1/20; A01M 1/00; A01N 25/00; A01N 43/78; A01N 43/74; A01N 43/72; A01N 43/00; A01N 43/88; A01N 47/44; A01N 47/42; A01N 47/40; A01N 47/00; A01N 51/00
See application file for complete search history.

(56) References Cited

U.S. PATENT DOCUMENTS

| | | |
|---|---|---|
| 2007/0078171 A1 | 4/2007 | Andersch et al. |
| 2007/0249498 A1 | 10/2007 | Van Der Drift |
| 2008/0234331 A1 | 9/2008 | Fellmann et al. |
| 2010/0317520 A1 | 12/2010 | Ikeda et al. |
| 2014/0020610 A1 | 1/2014 | Sakamoto et al. |

FOREIGN PATENT DOCUMENTS

| | | |
|---|---|---|
| JP | 2008501353 A | 1/2008 |
| JP | 2011016783 A | 1/2011 |
| JP | 2014037401 A | 2/2014 |
| WO | 2005036966 A1 | 4/2005 |
| WO | 2005120226 A2 | 12/2005 |
| WO | 2007054214 A1 | 5/2007 |

OTHER PUBLICATIONS

Int'l Search Report dated Jul. 14, 2015 in Int'l Application No. PCT/JP2015/061329 (English Translation).
Int'l Preliminary Report on Patentability dated Oct. 25, 2016 in Int'l Application No. PCT/JP2015/061329 (English Translation).

*Primary Examiner* — Christopher J. Novosad
(74) *Attorney, Agent, or Firm* — Panitch Schwarze Belisario & Nadel LLP

(57) ABSTRACT

A method for controlling arthropod pests includes: step a): a step of forming furrows in the soil; step b): a step of placing, in the furrows formed in the previous step, seeds retaining one or more neonicotinoid compounds selected from group I, on the surface or in the interior, and a step of applying an aqueous dispersion or an aqueous solution containing one or more neonicotinoid compounds selected from group I to the furrows formed in the previous step; and step c): a step of covering the furrows. In step b above group I is a group selected from clothianidin, thiamethoxam, imidacloprid, and thiacloprid.

2 Claims, No Drawings

METHOD FOR CONTROLLING ARTHROPOD PESTS

CROSS-REFERENCE TO RELATED APPLICATION

This application is a Section 371 of International Application No. PCT/JP2015/061329, filed Apr. 13, 2015, which was published in the Japanese language on Oct. 29, 2015, under International Publication No. WO 2015/163177 A1, and the disclosure of which is incorporated herein by reference.

TECHNICAL FIELD

The present invention relates to a method for controlling arthropod pests.

BACKGROUND ART

Regarding the method for preventing the damages caused by arthropod pests in crop cultivation, various methods are conventionally known (for example, Patent Citation 1 and Non Patent Citation 1).

On the other hand, there is known a method for protecting germinating seeds that have been treated with an agrochemical, by keeping one or more agrochemical-containing particles in the immediate vicinity of agrochemically treated seeds (for example, Patent Citation 2).
[Patent Citation 1] JP-A 2014-037401
[Patent Citation 2] JP-A 2008-501353
[Non Patent Citation 1] Handbook of Corn Insects, ISBN: 8-938522-76-0, 1999, Entomological Society of America.

DISCLOSURE OF INVENTION

Technical Problem

In regard to crop cultivation, as a result of global increases in the demand for crops, a variety of efforts have been made in order to increase the yield. Particularly, since the decrease in the yield of crops caused by arthropod pests has posed a problem, there is a demand for an excellent method for controlling arthropod pests.

Technical Solution

The inventors of the present invention conducted an investigation to find a method for controlling harmful living organisms, and as a result, the inventors found an excellent method for controlling arthropod pests.

That is, the present invention includes the following.

[1] A method for controlling arthropod pests, the method comprising:

Step A): a step of forming furrows in the soil;

Step B): a step of placing, in the furrows formed in the previous step, seeds retaining one or more neonicotinoid compounds selected from Group I (hereinafter, described as the present neonicotinoid compounds) on the surface or in the interior, and a step of applying an aqueous dispersion or an aqueous solution containing one or more neonicotinoid compounds selected from Group I to the furrows formed in the previous step; and Step (C): a step of covering the furrows, wherein Group I is a group consisting of clothianidin, thiamethoxam, imidacloprid, and thiacloprid.

[2] The method for controlling arthropod pests according to [1], wherein the seeds are corn seeds.

Advantageous Effects

The present invention provides an excellent method for controlling arthropod pests.

BEST MODE FOR CARRYING OUT THE INVENTION

Regarding the order of carrying out the present invention, Step A is followed by Step B, and subsequently Step C is performed. In regard to Step B, the step of placing seeds that retain the present neonicotinoid compounds on the surface or in the interior, and the step of applying an aqueous dispersion or an aqueous solution containing the present neonicotinoid compounds may be performed simultaneously, or may be performed separately. In a case in which the steps are performed separately, the seeds may be placed first, or the aqueous dispersion or the aqueous solution may be applied first.

The furrows formed in Step A are usually furrows that are provided linearly in the soil and have a V-shaped cross-section. The furrows are formed using an agricultural implement such as a hoe, or are formed by means of an attachment installed in a seeding machine.

The present neonicotinoid compounds used for the present invention are clothianidin, thiamethoxam, imidacloprid, and thiacloprid.

Among them, a preferred example of the present neonicotinoid compounds to be retained in the seeds is clothianidin. Furthermore, as the present neonicotinoid compounds to be included in the aqueous dispersion or the aqueous solution, clothianidin and/or imidacloprid is preferred, and clothianidin is more preferred.

According to the present invention, it is preferable to use clothianidin as the present neonicotinoid compound to be retained in the seeds, and to use clothianidin and/or imidacloprid as the present neonicotinoid compounds to be included in the aqueous dispersion or the aqueous solution. Furthermore, it is more preferable to use clothianidin as the present neonicotinoid compound to be retained in the seeds, and to use clothianidin as the present neonicotinoid compound to be included in the aqueous dispersion or the aqueous solution.

The present neonicotinoid compound to be retained in the seeds in Step B and the present neonicotinoid compound to be included in the aqueous dispersion or the aqueous solution applied to the furrows in Step B may be the same compound, or may be different compounds, and may be in the same dosage form or in different dosage forms.

Clothianidin is a known compound and is described in, for example, page 229 of "The Pesticide Manual—16$^{th}$ Edition (published by BCPC); ISBN 978-1-901396-18-8". Clothianidin is obtained as a commercially available preparation, or is obtained by producing the compound by a known method.

Thiamethoxam is a known compound and is described in, for example, page 1112 of "The Pesticide Manual—16$^{th}$ Edition (published by BCPC); ISBN 978-1-901396-18-8". Thiamethoxam is obtained as a commercially available preparation, or is obtained by producing the compound by a known method.

Imidacloprid is a known compound, and is described in, for example, page 645 of "The Pesticide Manual—16$^{th}$ Edition (published by BCPC); ISBN 978-1-901396-18-8".

Imidacloprid is obtained as a commercially available preparation, or is obtained by producing the compound by a known method.

Thiacloprid is a known compound and is described in, for example, page 1111 of "The Pesticide Manual—16$^{th}$ Edition (published by BCPC); ISBN 978-1-901396-18-8". Thiacloprid is obtained as a commercially available preparation, or is obtained by producing the compound by a known method.

The present neonicotinoid compound used for the present invention may be the present neonicotinoid compound itself; however, usually, the present neonicotinoid compound is formulated by mixing the compound with an appropriate solid carrier or an appropriate liquid carrier, and adding a surfactant or other auxiliary agents for formulation thereto as necessary.

Examples of the solid carrier include natural or synthetic minerals such as clay, kaolin, talc, bentonite, sericite, sulfur, activated carbon, calcium carbonate, diatomaceous earth, quartz, pumice, calcite, sepiolite, dolomite, olivine, pyroxene, amphibole, feldspar, silica, alumina, vermiculite, and pearlite; and fine particles of elastomers, plastics, ceramics, metals, sawdust, corncobs, coconut husks, and tobacco stems.

Examples of the liquid carrier include water, xylene, methanol, butanol, pentanol, benzyl alcohol, cyclohexanone, γ-butyrolactone, N-methylpyrrolidone, N-octylpyrrolidone, glycol diacetate, glycols, fatty acid dimethyl amides, fatty acids, and fatty acid esters. Furthermore, a mixture of two or more kinds of liquid carriers may also be used.

Examples of the surfactant include nonionic surfactants, cationic surfactants, anionic surfactants, and amphoteric surfactants, and one kind or two or more kinds of these surfactants are used.

Examples of the surfactant to be used include alkyl sulfates, alkyl sulfuric acid ester salts, alkyl sulfonates, alkyl aryl sulfonates, lignosulfonates, naphthalene sulfonates, phenol sulfonates, dibutyl naphthalene sulfonates, fatty alcohol sulfates, fatty acid alkyl aryl ethers and polyoxyethylene compounds thereof, polyethylene glycol ethers, polyethylene glycol fatty acid esters, polyhydric alcohol esters, sugar alcohol derivatives, and silicone-based surfactants.

Examples of the other auxiliary agents for formulation include an emulsifier, a dispersant, an antifoaming agent, a stabilizer, an antiseptic agent, a thickening agent, a humectant, an adhesive, and a coloring material.

According to the present invention, the present neonicotinoid compounds are retained on the surface or in the interior of seeds. The method for retaining the present neonicotinoid compounds in seeds may be any known method as long as the present neonicotinoid compounds can be retained on the surface or in the interior of seeds, and examples include a method of subjecting seeds to a smear treatment with a liquid preparation containing the present neonicotinoid compounds or an aqueous dilution of a solid or liquid preparation containing the present neonicotinoid compounds, a method of subjecting seeds to an immersion treatment with the same, a method of dust coating seeds with a solid preparation containing the present neonicotinoid compounds, and a method of forming seeds into a pellet form using a carrier containing the present neonicotinoid compounds.

Specific examples of such a preparation include a water-soluble powder, a wettable powder, water-dispersible granules, a soluble concentrate, microcapsules, an emulsifiable concentrate, a concentrated emulsion, a microemulsion, a suspoemulsion, an oil-miscible liquid, a suspension concentrate or a dry flowable, and a powder.

The amount of the present neonicotinoid compounds to be retained in the seeds according to the present invention may be varied as appropriate depending on the conditions for cultivation of crops, climate conditions, etc.; however, usually, the amount is 0.01 to 40 g, and preferably 0.05 to 10 g, per kilogram of seeds.

Examples of the method for placing seeds in Step B include a method of manually placing seeds in the furrows in Step B, and a method of placing seeds using a manually operated seeding machine or a mechanical seeding machine.

The aqueous dispersion or the aqueous solution of the present neonicotinoid compounds in Step B of the present invention is obtained by dispersing or dissolving the present neonicotinoid compounds or a preparation containing the present neonicotinoid compounds, in water. Preferably, an aqueous dispersion or an aqueous solution obtainable by dispersing or dissolving a water-soluble powder, a wettable powder, water-dispersible granules, a soluble concentrate, microcapsules, an emulsifiable concentrate, a concentrated emulsion, a microemulsion, a suspoemulsion, an oil-miscible liquid, a suspension concentrate or a dry flowable, all of which contain the present neonicotinoid compounds, in water is used.

In regard to Step B, the amount of the present neonicotinoid compounds to be used may be varied as appropriate depending on the conditions for cultivation of crops, climate conditions, etc.; however, the amount is usually 5 to 500 g, and preferably 10 to 400 g, per hectare of the soil in which furrows are formed.

In regard to Step B, the ratio of the amount of the present neonicotinoid compounds to be retained in the seeds and the amount of the present neonicotinoid compounds to be used per hectare of soil is from 1:100 to 100:1, and preferably from 1:10 to 10:1.

The amount of application of the aqueous dispersion or the aqueous solution in Step B may be varied as appropriate depending on the conditions of cultivation of crops, climate conditions, etc.; however, the amount of application is usually 10 to 1000 liters, preferably 50 to 500 liters, and more preferably 50 to 300 liters, per hectare of the soil in which furrows are formed.

The method for applying the aqueous dispersion or the aqueous solution in Step B may be any method that can apply the aqueous dispersion or the aqueous solution to furrows, and particularly, spraying, dripping or drenching is preferred.

Specific examples of the arthropod pests that can be controlled by the present invention include the following.

Hemipteran pests: planthoppers such as *Laodelphax striatellus*; leafhoppers such as *Empoasca onukii*; aphids such as *Aphis gossypil*, *Myzus persicae*, *Brevicoryne brassicae*, *Macrosiphum euphorbiae*, *Aulacorthum solani*, *Rhopalosiphum padi*, *Acyrthosiphon pisum*, *Rhopalosiphum nymphaeae*, *Aphis naturtii*, and *Aphis fabae*; pentatomids such as *Halyomorpha mista* and *Lygus lineolaris*; and whiteflies such as *Trialeurodes vaporariorum*, *Bemisia tabaci*, and *Bemisia argentifolii*.

Lepidoptexan pests: pyralids such as *Ostrinia furnacalis*, *Hellula undalis*, *Pediasia teterrellus*, and *Ostrinia nubilaris*; noctuids such as *Spodoptera litura*, *Agrotis ipsilon*, and *Mythimna separata*; pierid butterflies such as *Pieris rapae*; tortricids such as *Tetramoera schistaceana*; ermine moths such as *Plutella xylostella*; and gelechiids such as *Phthorimaea operculella*.

Thysanopteran pests: thrips such as *Frankliniella occidentalis*, *Thrips parmi*, *Scirtothrips dorsalis*, *Thrips tabaci*, *Frankliniella intonsa*, and *Frankliniella fusca*.

Dipteran pests: anthomylid flies such as *Delia platura* and *Delia antiqua*; leafminer flies such as *Liriomyza sativae*, *Liriomyza trifolii*, and *Chromatomyia horticola*.

Coleopteran pests: corn rootworms (*Diabrotica* spp.) such as *Diabrotica virgifera* virgifera and *Diabrotica undecimpunctata* howardi; scarab beetles such as *Anomala cuprea*, *Anomala albopilosa*, *Anomala rufocuprea*, and *Popillia japonica*; weevils such as *Sphenophorus uniformis*; leaf beetles such as *Aulacophora femoralis* and *Leptinotarsa decemlineata*; and click beetles (*Agriotes* spp.).

The present invention is preferably applicable to hemipteran pests, lepidopteran pests, dipteran pests, and coleopteran pests, and is particularly preferably applicable to *Agriotes* spp., *Diabrotica* spp., noctuids, anthomylid flies, and aphids.

Examples of the crops to which the present invention can be applied include cereal crops, pseudocereal crops, legumes, rapeseed, sugar beet, cotton, sunflower, and tobacco. Examples of the cereal crops include corn, sorghum, wheat family (wheat, barley, rye, oat, and the like), rice, and millet. Examples of the pseudocereal crops include buckwheat, amaranthus, and quinoa. Examples of the legumes include soybean and peanut. The present invention is preferably applicable to cereal crops and legumes. The present invention is more preferably applicable to corn, wheat family, sorghum, and soybean. The present invention is even more preferably applicable to corn or soybean.

According to the present invention, the crop seeds are not limited as long as the seeds of a crop variety that is generally cultivated are used. Plants of such a variety also include plants to which one or more useful traits have been imparted by a classical breeding method or a genetic recombination technology, and stacked GM plants obtained by crossbreeding those plants.

Examples of such useful traits include resistance to herbicides, resistance to pests, resistance to diseases, stress resistance, and quality improvement of crops having modified compositions of fatty acid residues of oils and fats.

EXAMPLES

Next, the present invention will be further described by way of the following Formulation Examples and Test Examples; however, the present invention is not intended to be limited to these Examples. Meanwhile, in the following Examples, unless particularly stated otherwise, the unit parts represents parts by weight, and the Formulation Examples represent Formulation Examples in the case of retaining the present neonicotinoid compounds in the seeds, and Formulation Examples in the case of applying an aqueous dispersion or an aqueous solution to furrows.

Formulation Example 1

20 parts of clothianidin is added to a mixture obtained by mixing 4 parts of sodium lauryl sulfate, 2 parts of calcium lignin sulfonate, 20 parts of a fine powder of synthetic hydrated silicon oxide and 54 parts of diatomaceous earth, and the mixture is thoroughly stirred and mixed. Thus, a wettable powder is obtained.

Formulation Example 2

100 parts of a mixture obtained by mixing 40 parts of clothianidin, 30 parts of white carbon containing 50 parts of an ammonium polyoxyethylene alkyl ether sulfate salt, and water for the balance, is finely pulverized by a wet pulverization method, and thereby a suspension concentrate is obtained.

Formulation Example 3

40 parts of clothianidin, 5 parts of propylene glycol (manufactured by Nacalai Tesque, Inc.), 5 parts of SOPROPHOR FLK (manufactured by Rhodia Nicca, Ltd.), 0.2 parts of ANTIFOAM C EMULSION (manufactured by Dow Corning Corporation), 0.3 parts of PROXEL GXL (manufactured by Arch Chemicals, Inc.), and 49.5 parts of ion-exchanged water are mixed at the aforementioned proportions, and a slurry is prepared. Into 100 parts of this slurry, 150 parts of glass beads ($\phi$=1 mm) are introduced, and the slurry is pulverized for 2 hours while being cooled with cooling water. After pulverization, the glass beads are removed by filtration, and thus a suspension concentrate is obtained.

Formulation Example 4

28.5 parts of an aqueous solution containing 2 parts of polyvinyl alcohol, and 20 parts of clothianidin are mixed, and the mixture is finely pulverized by a wet pulverization method. Subsequently, 41.5 parts of an aqueous solution containing 0.05 parts of xanthan gum and 0.1 parts of aluminum magnesium silicate is added to the mixture, and 10 parts of propylene glycol is further added thereto. The mixture is stirred and mixed, and thus a suspension concentrate is obtained.

Test Example 1

An aqueous dispersion prepared by adding water to a clothianidin wettable powder (47.8% wettable powder, trade name: NipsIt INSIDE, manufactured by Valent USA Corporation) was retained in the seeds of corn by a smear treatment using a seed treating machine (trade name: HEGE 11, manufactured by Wintersteiger AG), such that the amount of clothianidin to be retained per kilogram of seeds was 0.9 g.

A plastic container having a diameter of 7 cm and a depth of 12 cm was filled with soil, and V-shaped furrows having a depth of 3 cm were formed at the soil surface. At the combinations indicated in Table 1, one kernel of the corn seed was placed in a furrow, and subsequently, an aqueous solution obtained by dissolving a clothianidin water soluble powder (16% water soluble powder, trade name: DANTOTSU water soluble powder, manufactured by Sumitomo Chemical Co., Ltd.), an aqueous dispersion obtained by dispersing an imidacloprid wettable powder (50% water-dispersible granules, trade name: ADMIRE water-dispersible granules, manufactured by Bayer CropScience AG), clothianidin granules (0.5% granules, trade name: DANTOTSU granules, manufactured by Sumitomo Chemical Co., Ltd.), or imidacloprid granules (1% granules, trade name: ADMIRE granules, manufactured by Bayer CropScience AG) was applied into the furrows at the amounts described in Table 1. The furrows were covered by gathering the soil from a side of each furrow.

In this state, corn was grown in a greenhouse.

Ten days after the application of the seeds retaining clothianidin and the aqueous dispersion, aqueous solution or granules containing the present neonicotinoid compounds, ten 3-instar larvae of *Mythimna separata* were released per stem of corn. This is referred to as treated section.

On the other hand, furrows were formed by the method described above, and one kernel of corn seed that did not retain the present neonicotinoid compounds was placed in a furrow. The furrows were covered. In this state, corn was grown in a greenhouse. Ten days after the corn seeds were sown, ten 3-instar larvae of *Mythimna separata* were released per stem of corn. This is referred to as untreated section.

One day after the insect release, the number of healthy *Mythimna separata* and the number of dead *Mythimna separata* were examined with respect to the total number of *Mythimna separata* released, and the preventive value was calculated using the following expression.

Preventive value=100×(1−A/B)

A: Number of healthy *Mythimna separata* at the treated section at the time of examination
B: Number of healthy *Mythimna separata* at the untreated section at the time of examination

TABLE 1

| Present neonicotinoid compounds retained in seeds | Amount retained (g/1 kg of seeds) | Preparation applied to furrows | Amount applied (g/ha) | Preventive value |
|---|---|---|---|---|
| Clothianidin | 0.9 | Clothianidin water-soluble powder | 50 | 88 |
| Clothianidin | 0.9 | Clothianidin granules | 50 | 68 |
| Clothianidin | 0.9 | Clothianidin water-soluble powder | 150 | 94 |
| Clothianidin | 0.9 | Clothianidin granules | 150 | 70 |
| Clothianidin | 0.9 | Imidacloprid wettable powder | 50 | 73 |
| Clothianidin | 0.9 | Imidacloprid granules | 50 | 62 |
| Clothianidin | 0.9 | Imidacloprid wettable powder | 150 | 82 |
| Clothianidin | 0.9 | Imidacloprid granules | 150 | 70 |

From the results described above, it is obvious that an excellent arthropod pest controlling effect is obtained by the present invention.

Test Example 2

An aqueous dispersion prepared by adding water to a clothianidin wettable powder (47.8% wettable powder, trade name: NipsIt INSIDE, manufactured by Valent USA Corporation) was retained in the seeds of corn by a smear treatment using a seed treating machine (trade name: HEGE 11, manufactured by Wintersteiger AG), such that the amount of clothianidin to foe retained per kilogram of seeds was 0.9 g.

A plastic container having a diameter of 7 cm and a depth of 12 cm was filled with soil, and V-shaped furrows having a depth of 3 cm were formed at the soil surface. Ten larvae of *Delia platura* were released into the furrows, and also, one kernel of the corn seed was placed in the furrows. Subsequently, an aqueous dispersion prepared by adding water to an imidacloprid wettable powder (50% water-dispersible granules, trade name: ADMIRE water-dispersible granules, manufactured by Bayer CropScience AG) was applied into the furrows such that the amount of application of imidacloprid per hectare was 50 g. The furrows were covered by gathering the soil from a side of each furrow.

Corn was grown in a greenhouse. This is referred to as treated section.

On the other hand, furrows were formed by the method described above, ten larvae of *Delia platura* were released into the furrows, and also one kernel of corn seed that did not retain the present neonicotinoid compounds was placed in a furrow. The furrows were covered. Corn was grown in a greenhouse. This is referred to as untreated section.

Ten days after the seeds were scattered, the number of pupae of *Delia platura* living in the cup was counted, and the preventive value was calculated using the following expression.

Preventive value=100×(1−A/B)

A: Number of pupae at the treated section
B: Number of pupae at the untreated section

TABLE 2

| Present neonicotinoid compounds retained in seeds | Amount retained (g/1 kg of seeds) | Present neonicotinoid compounds applied to furrows | Amount applied (g/ha) | Preventive value |
|---|---|---|---|---|
| Clothianidin | 0.9 | Imidacloprid | 50 | 70 |

As a result, an excellent harmful living organism controlling effect was obtained in the treated section.

Test Example 3

Corn was grown by the same method as that used in Test Example 2, except that the treatment of corn seeds with the present neonicotinoid compounds and the application of the present neonicotinoid compounds into the furrows were performed at the combinations indicated in Table 3. The results are presented in Table 3. A arthropod pest controlling effect was recognized at the treated section.

TABLE 3

| Present neonicotinoid compounds retained in seeds | Amount retained (g/1 kg of seeds) | Present neonicotinoid compounds applied to furrows | Amount applied (g/ha) | Preventive value |
|---|---|---|---|---|
| Clothianidin | 0.9 | Clothianidin | 50 | 90 |
| Imidacloprid | 0.9 | Clothianidin | 50 | 77 |
| Thiamethoxam | 0.9 | Clothianidin | 50 | 77 |
| Thiacloprid | 0.9 | Clothianidin | 50 | 70 |
| Clothianidin | 0.9 | Thiamethoxam | 50 | 83 |
| Clothianidin | 0.9 | Thiacloprid | 50 | 70 |

INDUSTRIAL APPLICABILITY

The present invention provides an excellent method for controlling arthropod pests in crop cultivation.

The invention claimed is:
1. A method for controlling arthropod pests, the method comprising:
Step A): a step of forming furrows in the soil;

Step B): a step of placing, in the furrows formed in the previous step, seeds retaining one or more neonicotinoid compounds selected from Group I, on a surface or in an interior of the seeds, and a step of applying an aqueous dispersion or an aqueous solution containing one or more neonicotinoid compounds selected from Group I to the furrows formed in the previous step; and Step C): a step of covering the furrows, wherein Group I is a group consisting of clothianidin, thiamethoxam, imidacloprid, and thiacloprid.

2. The method for controlling arthropod pests according to claim 1, wherein the seeds are corn seeds.

* * * * *